(12) United States Patent
Wu et al.

(10) Patent No.: US 11,115,487 B2
(45) Date of Patent: Sep. 7, 2021

(54) SERVER AND METHOD FOR SERVICE MATCHING AND RESOURCE MATCHING

(71) Applicant: FREE BIONICS TAIWAN INC., Hsinchu (TW)

(72) Inventors: Cheng-Hua Wu, Hsinchu (TW); Cheng Kuo Chen, New Taipei (TW); Chien-Yi Lai, Hsinchu (TW)

(73) Assignee: FREE BIONICS TAIWAN INC., Hsinchu (TW)

( * ) Notice: Subject to any disclaimer, the term of this patent is extended or adjusted under 35 U.S.C. 154(b) by 144 days.

(21) Appl. No.: 16/389,329

(22) Filed: Apr. 19, 2019

(65) Prior Publication Data

US 2019/0356747 A1   Nov. 21, 2019

Related U.S. Application Data

(60) Provisional application No. 62/674,243, filed on May 21, 2018.

(51) Int. Cl.
*G06F 15/173* (2006.01)
*H04L 29/08* (2006.01)
*G16H 40/20* (2018.01)

(52) U.S. Cl.
CPC .............. *H04L 67/24* (2013.01); *H04L 67/16* (2013.01); *H04L 67/26* (2013.01); *G16H 40/20* (2018.01)

(58) Field of Classification Search
CPC ......... H04L 67/24; H04L 67/16; H04L 67/26; G16H 40/20
USPC ........................................................ 709/223
See application file for complete search history.

(56) References Cited

U.S. PATENT DOCUMENTS

| | | | |
|---|---|---|---|
| 8,867,070 B2* | 10/2014 | Jazayeri ................ | G06F 3/1238 358/1.15 |
| 2007/0208837 A1* | 9/2007 | Tian ...................... | G06F 3/1226 709/223 |
| 2014/0036314 A1* | 2/2014 | Otsuka .................. | G06F 3/1296 358/1.15 |
| 2015/0039357 A1* | 2/2015 | Segal .................... | G06Q 10/10 705/5 |
| 2019/0220715 A1* | 7/2019 | Park ...................... | G16H 40/67 |

* cited by examiner

*Primary Examiner* — Alan S Chou
(74) *Attorney, Agent, or Firm* — WPAT, P.C.; Anthony King

(57) ABSTRACT

The present disclosure provides a server and a method for service matching and resource matching. The server stores a first resource available information and a second resource available information. The server receives a user request from a user device and determines a resource matching information according to the first resource available information and the second resource available information in response to the user request. The server transmits the resource matching information to the user device.

14 Claims, 17 Drawing Sheets

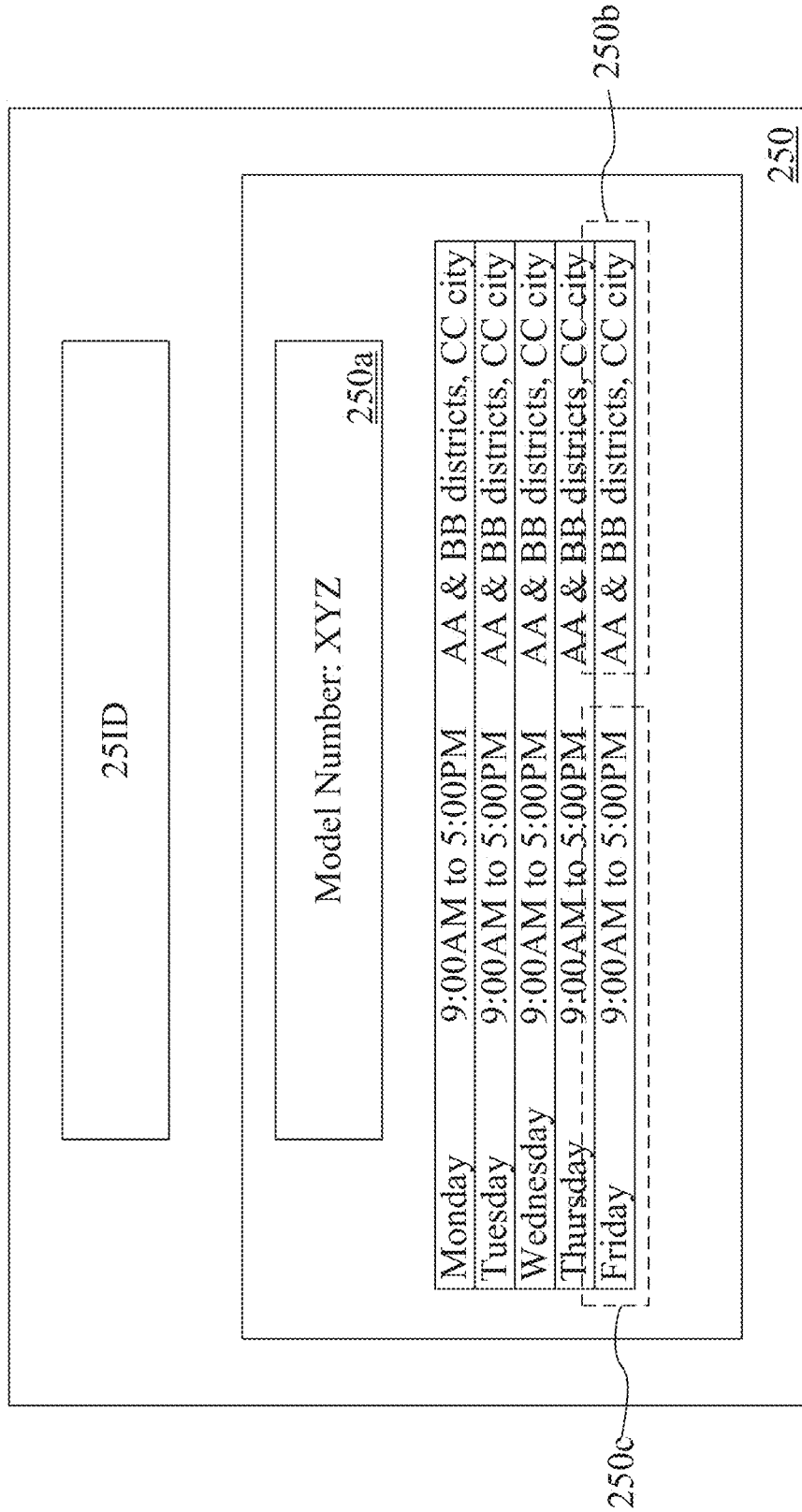

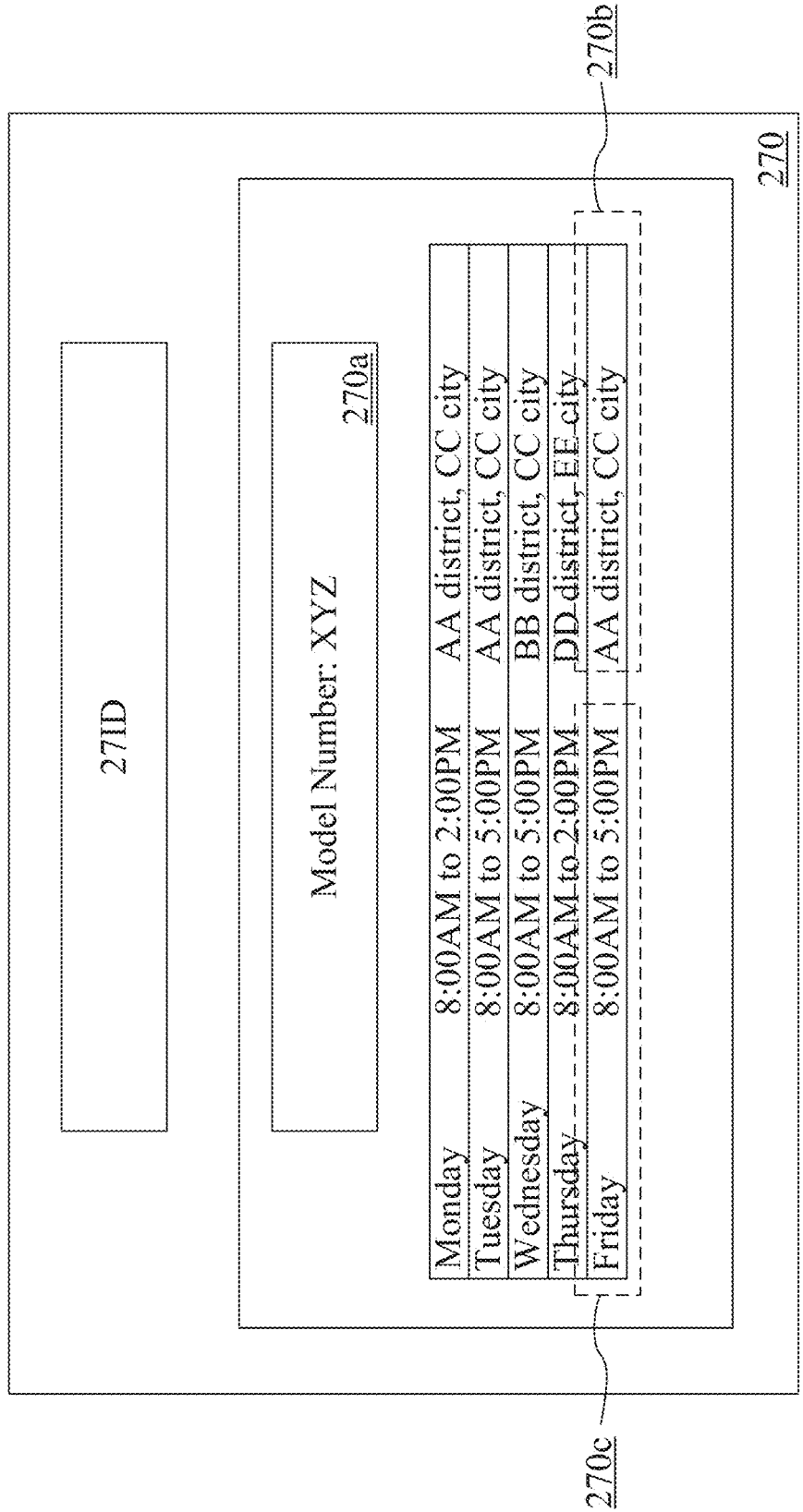

231D

Equipment request: XYZ  230a
Location request: AA district, CC city  230b
Time request: 10:00AM to 12:00PM Friday  230c

| | |
|---|---|
| Equipment user: | 231D |
| Equipment owner: | 251D |
| Equipment operator: | 271D |
| Location matching info.: | AA district, CC city |
| Time matching info.: | 10:00AM to 12:00PM Friday |
| Equipment matching info.: | XYZ |

```
        ┌─────────────────────┐
        │  Optional Operation │
        └──────────┬──────────┘
                   ▼
┌───────────────────────────────────────────┐
│ Receiving a service comment information   │
│ from one of the user, the first service   │
│ provider and the second service provider  │
│                                      S308 │
└───────────────────────────────────────────┘

┌─────────────────────┐
        │  Optional Operation │
        └──────────┬──────────┘
                   ▼
┌───────────────────────────────────────────┐
│ Receiving an equipment utilization log    │
│ from a service equipment corresponding    │
│ to the service matching information       │
│                                      S309 │
└───────────────────────────────────────────┘
```

FIG. 3C

SERVER AND METHOD FOR SERVICE MATCHING AND RESOURCE MATCHING

PRIORITY CLAIM AND CROSS-REFERENCE

This application claims priority of U.S. provisional application Ser. No. 62/674,243 filed on May 21, 2018, which is incorporated by reference in its entirety.

TECHNICAL FIELD

The present disclosure relates generally to a server and a method for information matching, more particularly, to a server and a method for service information matching and resource information matching.

DISCUSSION OF THE BACKGROUND

In a conventional matching system, only one provider and one user are involved. Therefore, the flexibility of using the matching system is very limited.

In particular, as for some precision equipment, since the operations may be complicated, an inappropriate operation may cause danger to its user. As a result, a trained operator is required for operating the precision equipment.

However, in some circumstances, the owner of the precision equipment and the trained operator for operating the precision equipment are different. Accordingly, the conventional matching system is insufficient.

SUMMARY

Embodiments of the present disclosure provide a method of service matching. The method includes: receiving a first service available information and a second service available information from a first service provider and a second service provider respectively; receiving service request information from a user; matching the service request information with the first service available information and the second service available information for obtaining a service matching information; and transmitting the service matching information to the user, the first service provider and the second service provider.

Embodiments of the present disclosure also provide a resource matching method for use in a server. The method includes: storing, by the server, a first resource available information and a second resource available information; receiving, by the server, a user request from a user device; determining, by the server, a resource matching information according to the first resource available information and the second resource available information in response to the user request; and transmitting, by the server, the resource matching information to the user device.

Some embodiments of the present disclosure provide a server. The server includes a storage, a transceiver and a processor. The storage, the transceiver and the processor are electrically coupled. The storage stores a first resource available information and a second resource available information. The transceiver receives a user request from a user device. The processor determines a resource matching information according to the first resource available information and the second resource available information in response to the user request. The transceiver transmits the resource matching information to the user device.

The foregoing has outlined rather broadly the features and technical advantages of the present disclosure in order that the detailed description of the disclosure that follows may be better understood. Additional features and advantages of the disclosure will be described hereinafter, and form the subject of the claims of the disclosure. It should be appreciated by those skilled in the art that the conception and specific embodiment disclosed may be readily utilized as a basis for modifying or designing other structures or processes for carrying out the same purposes of the present disclosure. It should also be realized by those skilled in the art that such equivalent constructions do not depart from the spirit and scope of the disclosure as set forth in the appended claims.

BRIEF DESCRIPTION OF THE DRAWINGS

A more complete understanding of the present disclosure may be derived by referring to the detailed description and claims when considered in connection with the Figures, where like reference numbers refer to similar elements throughout the Figures, and:

Aspects of the present disclosure are best understood from the following detailed description when read with the accompanying figures. It is noted that, in accordance with the standard practice in the industry, various features are not drawn to scale. In fact, the dimensions of the various features may be arbitrarily increased or reduced for clarity of discussion.

FIG. 2C is a schematic view of the first resource available information in accordance with some embodiments of the present disclosure.

FIG. 2D is a schematic view of the second resource available information in accordance with some embodiments of the present disclosure.

FIG. 2E is a schematic view of the user request in accordance with some embodiments of the present disclosure.

FIG. 2H is a schematic view of the resource matching information in accordance with some embodiments of the present disclosure.

FIGS. 3A to 3C are flowchart diagrams in accordance with some embodiments of the present disclosure.

DETAILED DESCRIPTION

Figure 1A:
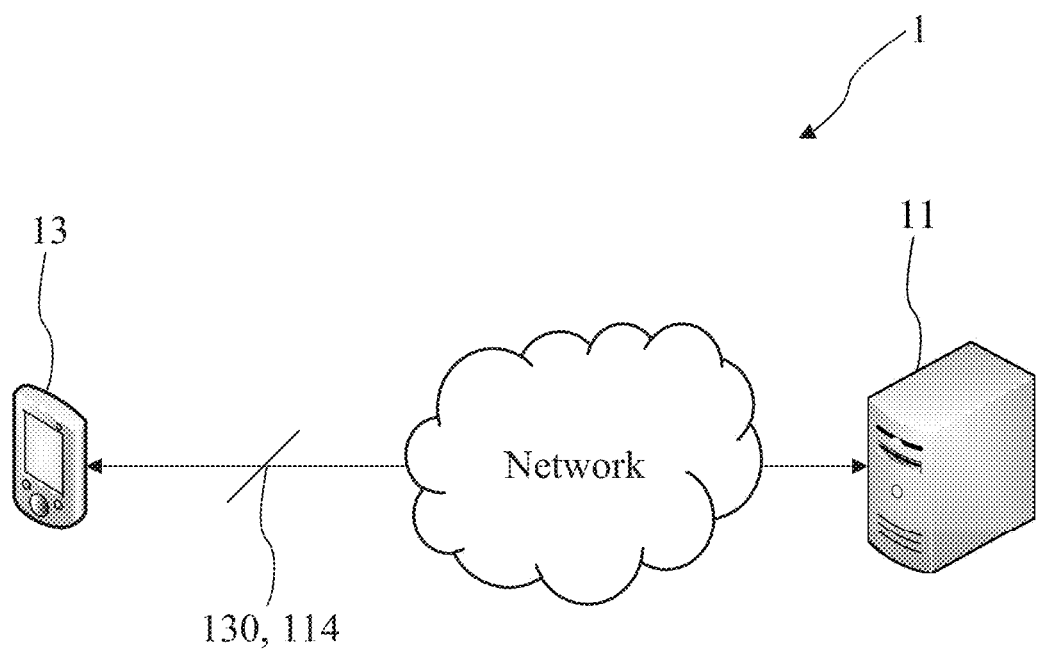
FIG. 1A is a schematic view of the matching system in accordance with some embodiments of the present disclosure.

Embodiments, or examples, of the disclosure illustrated in the drawings are now described using specific language. It shall be understood that no limitation of the scope of the disclosure is hereby intended. Any alteration or modification of the described embodiments, and any further applications of principles described in this document, are to be considered as normally occurring to one of ordinary skill in the art to which the disclosure relates. Reference numerals may be repeated throughout the embodiments, but this does not necessarily mean that feature(s) of one embodiment apply to another embodiment, even if they share the same reference numeral.

It shall be understood that, although the terms first, second, third, etc. may be used herein to describe various elements, components, regions, layers or sections, these elements, components, regions, layers or sections are not limited by these terms. Rather, these terms are merely used to distinguish one element, component, region, layer or section from another region, layer or section. Thus, a first element, component, region, layer or section discussed below could be termed a second element, component, region, layer or section without departing from the teachings of the present inventive concept.

The terminology used herein is for the purpose of describing particular example embodiments only and is not intended to be limited to the present inventive concept. As used herein, the singular forms "a," "an" and "the" are intended to include the plural forms as well, unless the context clearly indicates otherwise. It shall be further understood that the terms "comprises" and "comprising," when used in this specification, point out the presence of stated features, integers, steps, operations, elements, or components, but do not preclude the presence or addition of one or more other features, integers, steps, operations, elements, components, or groups thereof.

Figure 1B:
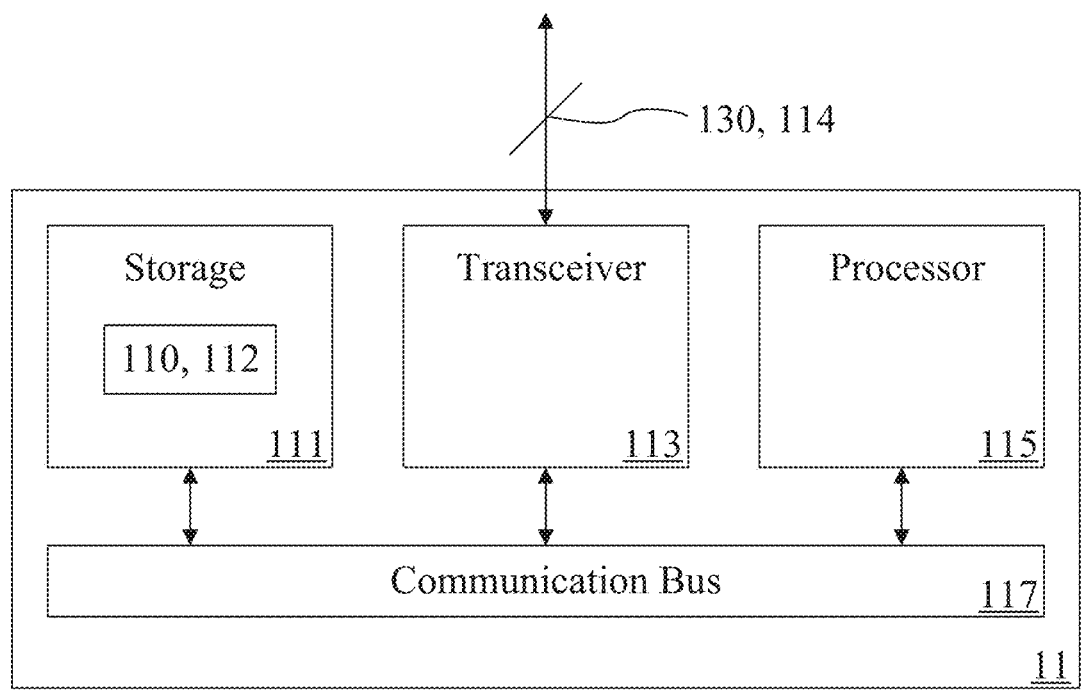
FIG. 1B is a block diagram of the server in accordance with some embodiments of the present disclosure.

FIG. 1A illustrates schematic view of a matching system 1 according to an embodiment of the present disclosure. The matching system 1 includes a server 11 and a user device 13. The server 11 and the user device 13 communicate with each other via network. FIG. 1B is a block diagram of the server 11 according to the embodiment of the present disclosure. The server 11 includes a storage 111, a transceiver 113 and a processor 115. The storage 111 stores a first resource available information 110 and a second resource available information 112.

As shown in FIG. 1B, the storage 111, the transceiver 113 and the processor 115 are electrically coupled through a communication bus 117 allowing the processor 115 to control the transceiver 113 to transmit and/or receive information, and to access information stored in the storage 111. The interactions between the individual elements will be further described hereinafter.

In some embodiments, when a user who needs a designated resource, the user uses the user device 13 to transmit a user request 130 to the server 11. Subsequently, the transceiver 113 of the server 11 receives the user request 130 from the user device 13, and then the processor 115 of the server 11 determines a resource matching information 114 according to the first resource available information 110 and the second resource available information 112 in response to the user request 130.

In detail, in some embodiments, the user request 130 may be used for requesting the designated resource. The first resource available information 110 and the second resource available information 112 may include available information of the designated resource. More specifically, the first resource available information 110 may include the available information of the designated resource provided by a resource provider, and the second resource available information 112 may include the available information of the designated resource provided by another resource provider.

Accordingly, based on the user request 130, the first resource available information 110 and the second resource available information 112, the processor 115 of the server 11 determines the resource matching information 114 which indicates whether the designated resource of the user request 130 is available according to the available information of the designated resource of the first resource available information 110 and the second resource available information 112.

After the processor 115 of the server 11 determines the resource matching information 114, the transceiver 113 of the server 11 transmits the resource matching information 114 to the user device 13 for notifying the user device 13 of whether the designated resource is available or not.

It should be noted that, in some embodiments, the resource matching information 114 may be positive (i.e., may be used for notifying the user device 13 of that the designated resource is available) while the designated resource of the user request 130 is determined to be available according to both of the available information of the designated resource of the first resource available information 110 and the available information of the designated resource of the second resource available information 112.

On the other hand, the resource matching information 114 may be negative (i.e., may be used for notifying the user device 13 of that the designated resource is not available) while the designated resource of the user request 130 is determined to be not available according to at least one of the available information of the designated resource of the first resource available information 110 and the available information of the designated resource of the second resource available information 112.

For example, the designated resource may include an equipment and a service of the equipment. The first resource available information 110 may include the available information of the equipment provided by an equipment owner. The second resource available information 112 may include the available information of the service provided by an equipment operator.

Accordingly, when the user uses the user device 13 to transmit the user request 130 to the server 11 for request the equipment and the service, the processor 115 may determines the resource matching information 114 according to the available information of the first resource available information 110 and the available information of the second resource available information 112.

In detail, when the available information of the first resource available information 110 and the available information of the second resource available information 112 fulfill the user request 130, the processor 115 of the server 11 determines the resource matching information 114 for notifying the user device 13 of that the equipment and the service are available as the user's request.

On the other hand, when one the available information of the first resource available information 110 and the available information of the second resource available information 112 cannot fulfill the user request 130, the processor 115 of the server 11 determines the resource matching information 114 for notifying the user device 13 of that the equipment or the service may not be available as the user's request.

Figure 2A:
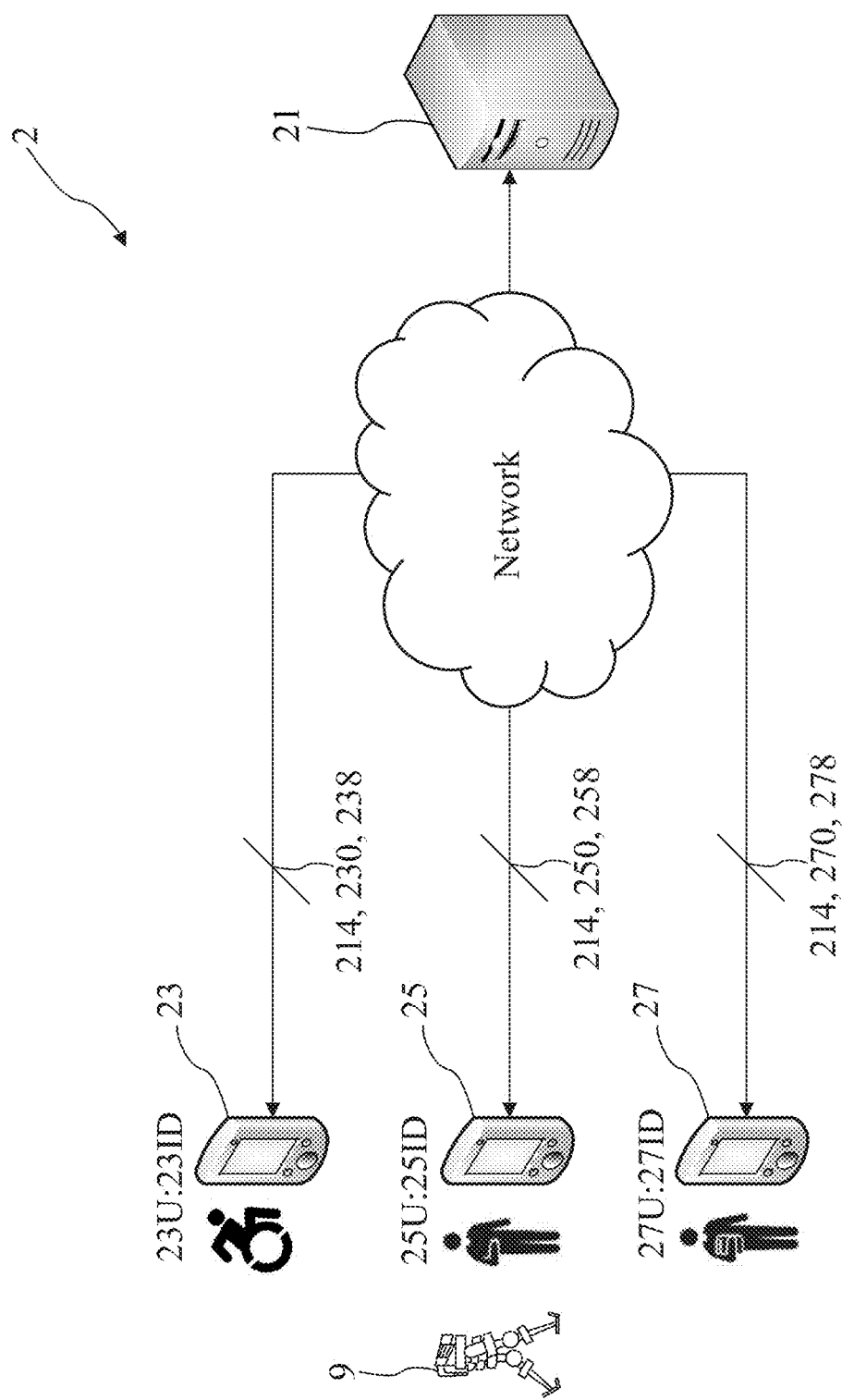
FIG. 2A is a schematic view of the matching system in accordance with some embodiments of the present disclosure.
Figure 2B:
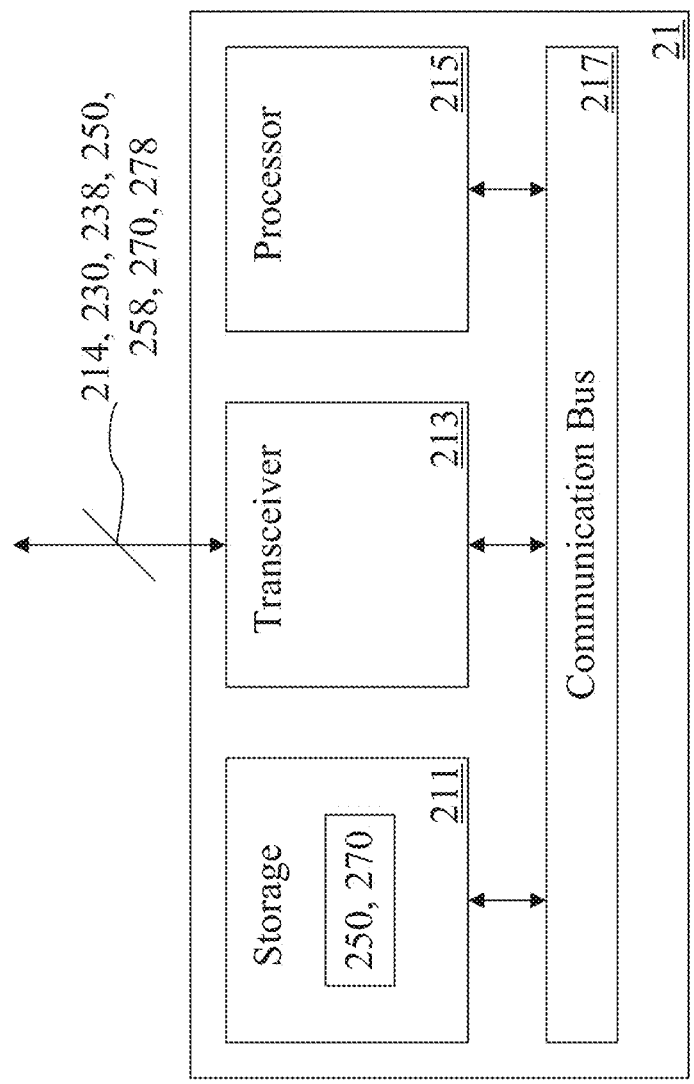
FIG. 2B is a block diagram of the server in accordance with some embodiments of the present disclosure.

FIG. 2A illustrates schematic view of a matching system 2 according to an embodiment of the present disclosure. The matching system 2 includes a server 21, a user device 23, a first client device 25 and a second client device 27. The server 21 communicates with the user device 23, the first client device 25 and the second client device 27 via network. FIG. 2B is a block diagram of the server 21 according to the embodiment of the present disclosure. The server 21 includes a storage 211, a transceiver 213 and a processor 215.

As shown in FIG. 2B, the storage 211, the transceiver 213 and the processor 215 are electrically coupled through a communication bus 217 allowing the processor 215 to control the transceiver 213 to transmit and/or receive information, and to access information stored in the storage 211. The interactions between the individual elements will be further described hereinafter.

In some embodiments, the user device 23 may be used by a medical equipment user 23U who needs a medical equipment 9 (e.g., an exoskeleton robot) and a medical service (e.g., a training course of the exoskeleton robot) of the medical equipment 9. The first client device 25 may be used by a medical equipment owner 25U who owns the medical equipment 9. The second client device 27 may be used by a medical equipment operator 27U who is a certified trainer for providing a medical service of the medical equipment 9.

Before matching medical equipment and medical services with user, some procedures may be set up first. In particular, the medical equipment owner 25U uses the first client device 25 to download a matching application from the server 21, and then to apply for membership via the matching application at the server 21. The medical equipment operator 27U uses the second client device 27 to download the matching application from the server 21, and then to apply for membership via the matching application at the server 21 as well. After applying for the memberships successfully, the medical equipment owner 25U obtains an equipment owner identification 25ID with the first client device 25, and the medical equipment operator 27U obtains an equipment operator identification 27ID with the second client device 27.

The medical equipment owner 25U uses the first client device 25 to transmit a first resource available information 250 to the server 21. Please refer to FIG. 2C which is a schematic view of the first resource available information 250. The first resource available information 250 with the equipment owner identification 25ID may include a first equipment information 250a, a plurality of location information (as shown in FIG. 2C) and a plurality of time information (as shown in FIG. 2C) which correspond to the medical equipment 9.

In detail, the first equipment information 250a may include a model number of the medical equipment 9. The plurality of location information may include available locations that the medical equipment owner 25U can provide the medical equipment 9. The plurality of time information may include available time slots that the medical equipment owner 25U can provide the medical equipment 9. The plurality location information corresponds to the plurality time information.

The medical equipment operator 27U uses the second client device 27 to transmit a second resource available information 270 to the server 21. Please refer to FIG. 2D which is a schematic view of the second resource available information 270. The second resource available information 270 with the equipment operator identification 27ID may include a second equipment information 270a, a plurality of location information (as shown in FIG. 2D) and a plurality of time information (as shown in FIG. 2D) which correspond to the medical equipment 9.

In detail, the second equipment information 270a may include the model number of the medical equipment 9. The plurality of location information may include available locations that the medical equipment operator 27U can provide the medical service for operating the medical equipment 9. The plurality of time information may include available time slots that the medical equipment operator 27U can provide the medical service for operating the medical equipment 9. The plurality of location information corresponds to the plurality of time information.

Accordingly, the transceiver 213 of the server 21 receives the first resource available information 250 and the second resource available information 270 and the processor 215 of the server 21 stores the first resource available information 250 and the second resource available information 270 in the storage 211 for later use.

When the medical equipment user 23U needs a medical equipment with a medical service, the medical equipment user 23U uses the user device 23 to download the matching application form the server 21, and then to apply for membership via the matching application at the server 21. After applying for the membership successfully, the medical equipment user 23U obtains an equipment user identification 23ID with the user device 25.

Next, the medical equipment user 23U uses the user device 23 to transmit a user request 230 to the server 21. Please refer to FIG. 2E which is a schematic view of the user request 230. The user request 230 may include an equipment request 230a, a location request 230b and a time request 230c.

In detail, the equipment request 230a may be used for requesting the medical equipment 9 and the medical service of the medical equipment 9. The location request 230b may be used for requesting a location to use the medical equipment 9. The time request 230c may be used for requesting a time slot to use the medical equipment 9.

Accordingly, after the transceiver 213 of the server 21 receives the user request 230, the processor 215 of the server 21 can perform the matching of the medical equipment user, the medical equipment owner and the medical equipment operator.

In these embodiments, the processor 215 of the server 21 matches the user request 230 with the first resource available information 250. In detail, the processor 215 of the server 21 determines that the equipment request 230a matches a first equipment information 250a, the location request 230b matches a first location information 250b of the plurality of the location information and the time request 230c matches a first time information 250c of the plurality of the time information.

Therefore, the processor 215 of the server 21 creates a first list L1 based on the determination of that that the equipment request 230a matches the first equipment information 250a, the location request 230b matches the first location information 250b and the time request 230c matches the first time information 250c. Please refer to FIG. 2F which is a schematic view of the first list L1. The first list L1 at least records the medical equipment 9 of the medical equipment owner 25U.

Further, the transceiver 213 of the server 21 transmits the first list L1 to the user device 23. When the medical equipment user 23U selects the medical equipment 9 of the medical equipment owner 25U according to the first list L1, the user device 23 transmits a first response message 232 to the server 21.

On the other hand, the processor 215 of the server 21 matches the user request 230 with the second resource available information 270. In detail, the processor 215 of the server 21 determines that the equipment request 230a matches the second equipment information 270a, the location request 230b matches a second location information 270*b* of the plurality of the location information and the time request 230*c* matches a second time information 270*c* of the plurality of the time information.

Therefore, the processor 215 of the server 21 creates a second list L2 based on the determination of that that the use equipment request 230*a* matches the second equipment information 270*a*, the location request 230*b* matches the second location information 270*b* and the time request 230*c* matches the second time information 270*c*. Please refer to FIG. 2G which is a schematic view of the second list L2. The second list L2 at least records the equipment operator identification 27ID of the medical equipment operator 27U.

Further, the transceiver 213 of the server 21 transmits the second list L2 to the user device 23. When the medical equipment user 23U selects the medical equipment operator 27U according to the second list L2, the user device 23 transmits a second response message 234 to the server 21.

According to the first response message 232 and the second response message 234, the server 21 can be notified of that: (1) the medical equipment user 23U selects the medical equipment 9 of the medical equipment owner 25U with the equipment owner identification 25ID as the medical equipment provider; (2) the medical equipment user 23U selects the medical equipment operator 27U with the equipment operator identification 27ID as the medical service provider; (3) matched equipment information; (4) matched location information; and (5) matched time information.

Therefore the processor 215 of the server 21 determines a resource matching information 214 based on the first response message 232 and the second response message 234. Please refer to FIG. 2H which is a schematic view of the resource matching information 214. The resource matching information 214 includes the user identification 23ID, the equipment owner identification 25ID, the equipment operator identification 27ID, a location matching information, a time matching information and an equipment matching information.

After the processor 215 of the server 21 determines the resource matching information 214, the transceiver 213 of the server 21 transmits the resource matching information 214 to the user device 23, the first client device 25 and the second client device 27 for informing the medical equipment user 23U, the medical equipment owner 25U and the medical equipment operator 27U of the matching result.

According to the matching result, the medical equipment owner 25U can provide the medical equipment 9 at "AA district, CC city" during 10:00 AM to 12:00 PM on. Friday. The medical equipment operator 27U can assist the medical equipment user 23U to perform a training course of the medical equipment 9 at "AA district, CC city" during 10:00 AM to 12:00 PM on Friday.

In some embodiments, for confirming that the content of the resource matching information 214 is fulfilled, a confirmation scheme may be introduced. In detail, the resource matching information 214 transmitted to the user device 23, the first client device 25 and the second client device 27 may include different identifying codes (not shown), such as quick response (QR) codes, for the user device 23, the first client device 25 and the second client device 27 respectively.

Accordingly, the medical equipment user 23U may use the user device 23 to scan the identifying codes of the first client device 25 and the second client device 27 for generating a user confirmation message 238. The user device 23 then transmits the user confirmation message 238 to the server 21.

Similarly, the medical equipment owner 25U may use the first client device 25 to scan the identifying codes of the user device 23 and the second client device 27 for generating a first confirmation message 258. The first client device 25 then transmits the first confirmation message 258 to the server 21.

Similarly, the medical equipment operator 27U may use the second client device 27 to scan the identifying codes of the user device 23 and the first client device 25 for generating a second confirmation message 278. The second client device 27 then transmits the second confirmation message 278 to the server 21

Subsequently, the transceiver 213 of the server 21 receives the user confirmation message 238, the first confirmation message 258 and the second confirmation message 278 respectively from the user device 23, the first client device 25 and the second client device 27. Then, the processor 21 of the server 21 determines an execution information (not shown) according to the user confirmation message 238, the first confirmation message 258 and the second confirmation message 278. The execution information may be used for indicating that the content of the resource matching information 214 is achieved.

In some embodiments, after the content of the resource matching information 214 is fulfilled, feedback information (e.g., service comment information) may be used for facilitating the user experiences. In detail, after the content of the resource matching information 214 is fulfilled, the medical equipment user 23, the medical equipment owner 25 or the medical equipment operator 27 may transmit a resource utilization feedback (not shown) to the server 21. The transceiver 213 of the server 21 then receives the resource utilization feedback from one of the user device 23, the first client device 25 and the second client device 27. The resource utilization feedback may be scores for the content of the resource matching information 214.

For example, when the medical equipment user 23U is very satisfied with the medical equipment 9 provided by the medical equipment owner 25, the medical equipment user 23U may use the user device 23 to transmit a resource utilization feedback for scoring the medical equipment 9 of the medical equipment owner 25U as 5 of 5 stars. When the medical equipment user 23U is satisfied with the medical service provided by the medical equipment operator 27U, the medical equipment user 23U may use the user device 23 to transmit a resource utilization feedback for scoring the medical equipment operator 27U as 4 of 5 stars.

In some embodiments, during the training course of operating the medical equipment 9, the medical equipment 9 may generate an equipment utilization log (not shown) for recording the details of operations. After the training course, the medical equipment 9 may transmit the equipment utilization log to the server 21. Subsequently, the transceiver 213 of the server 21 receives the equipment utilization log from the medical equipment 9. The processor 215 of the server 21 stores the equipment utilization log in the storage 211 of the server 21 for analyzing purposes. For example, when the medical equipment 9 is the exoskeleton robot, the equipment utilization log may include log of cadence, pace, velocity, etc., which may be analyzed for adjusting the mechanisms of medical equipment 9.

In some embodiments, the medical equipment 9 of the medical equipment owner 25U may correspond to a first rank (not shown) and the first rank depends on the score of the medical equipment 9 of the medical equipment owner 25U. Accordingly, when the processor 215 of the server 21 creates the first list L1, item with high rank may be preferentially listed. In these embodiments, since the first rank of the medical equipment 9 of the medical equipment owner 25U is higher than other ranks of other items, the medical equipment 9 of the medical equipment owner 25U is preferentially listed in the first list L1.

In some embodiments, the first rank may be dynamically adjusted based on different weights applied for the first rank. Please refer to FIG. 2I which is a flowchart diagram of updating weights for ranking. In detail, there may be a plurality of variables (e.g., PT, Robot, Closing rate, Commenting rate, etc.) that affects the first rank, and each variable corresponds to one weight.

In some embodiments, variable of PT represents score of equipment operator, variable of Robot represents score of equipment, variable of Closing rate represents score of rate of cases which are fulfilled, and variable of Commenting rate represents score of rate of cases which are commented with text.

Figure 2F:
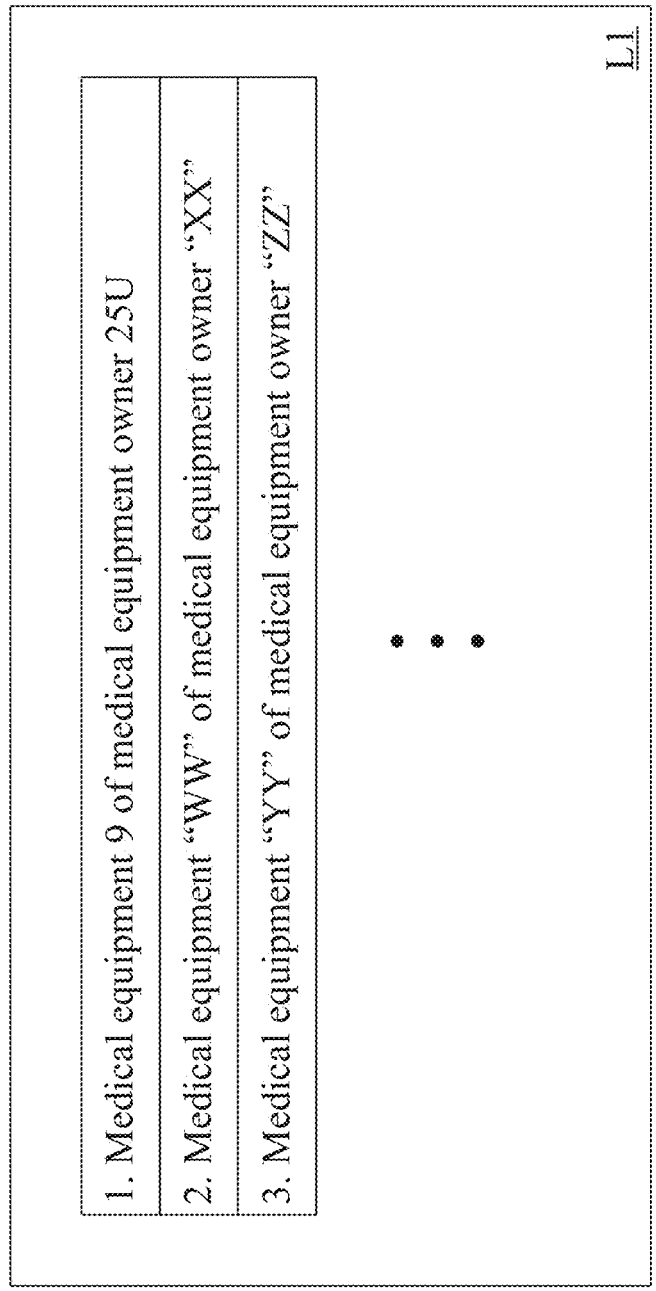
FIG. 2F is a schematic view of the first list in accordance with some embodiments of the present disclosure.
Figure 2G:
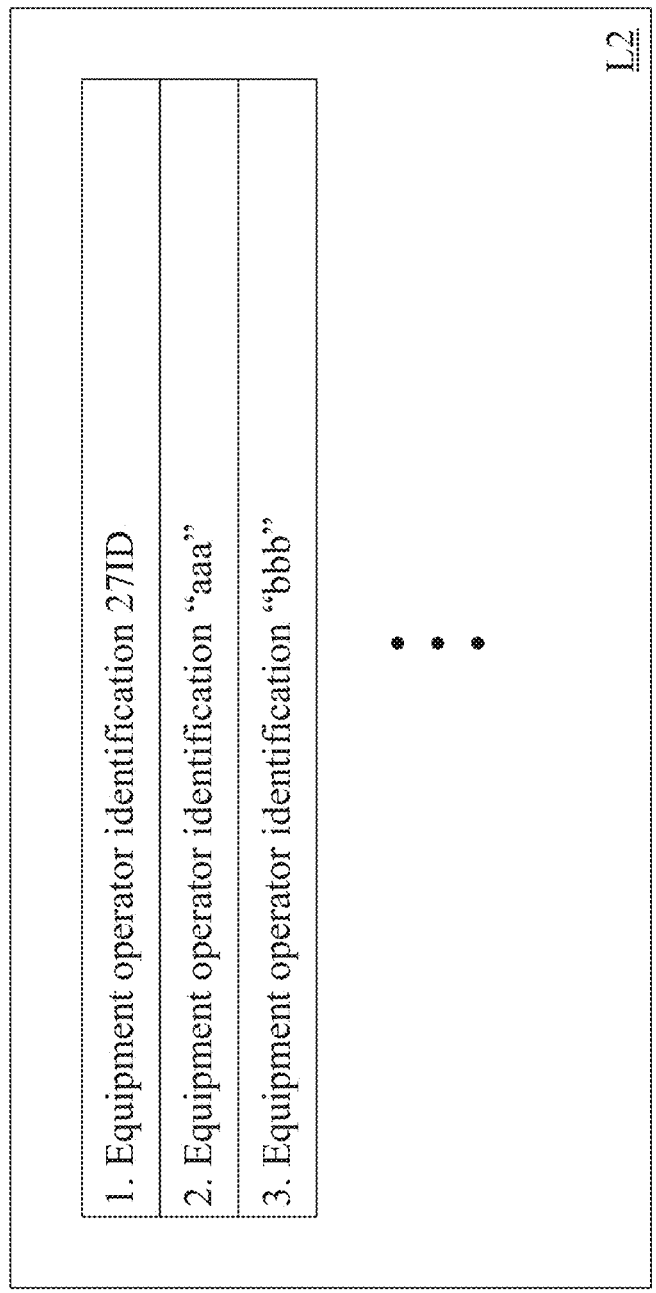
FIG. 2G is a schematic view of the second list in accordance with some embodiments of the present disclosure.
Figure 2I:
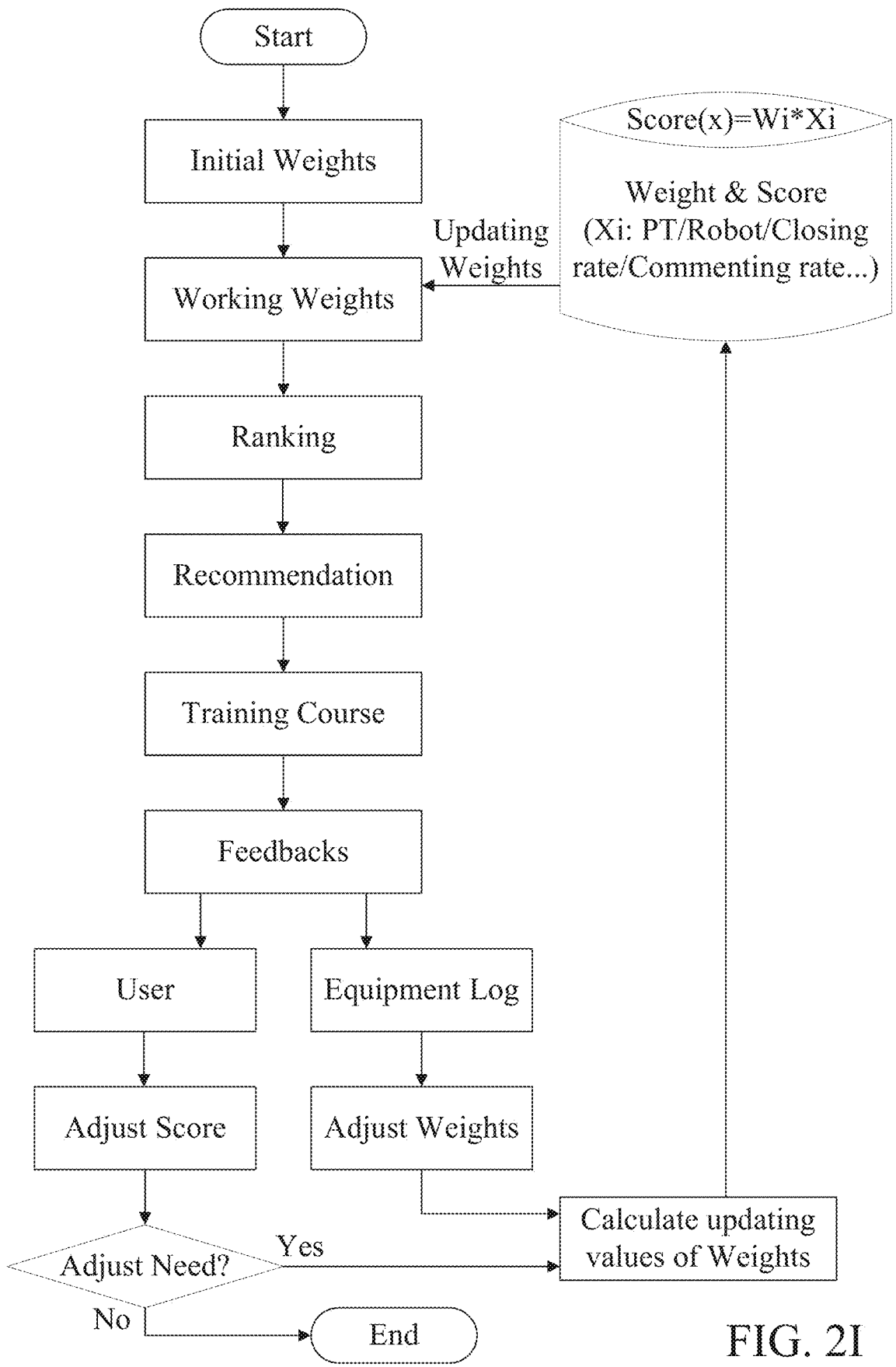
FIG. 2I is a flowchart diagram of updating weights for ranking in accordance with some embodiments of the present disclosure.

As shown in FIG. 2I, there are initial weights for the plurality of variables. The processor 215 of the server 21 calculates a Score(x) by the initial weights and the variables. Then, the calculated. Score(x) may be used for ranking the first rank. When the first rank is higher, the medical equipment 9 of the medical equipment owner 25U corresponding to the first rank may be preferably recommended in the first list L1.

Next, after the training course is completed, the medical equipment user 23U may use the user device 23 to transmit some feedbacks to the server 21. The feedbacks may be some adjusted scores corresponding to the mentioned variables. On the other hand, after the training course is completed, the equipment utilization log may be transmitted by the equipment and be used for adjusting the weights. Updating values of the weights may be calculated based on the adjustment of the score by the user and the adjustment of the weights. Then, the updating values of the weights may be used for updating the score which is used for ranking the first rank.

Similarly, the medical equipment operator 27U may correspond to a second rank (not shown) and the second rank depends on the score of the medical equipment operator 27U. Accordingly, when the processor 215 of the server 21 creates the second list L2, item with high rank may be preferentially listed. In these embodiments, since the second rank of the medical equipment operator 27U is higher than other ranks of other items, the medical equipment operator 27U is preferentially listed in the first list L2.

It should be noted that different ranks may be calculated for different medical equipment owned by different owners. Therefore, the first list may record a plurality of medical equipment with owners as shown in FIG. 2F. In addition, different ranks may be calculated for different medical equipment operator. Therefore, the second list may record a plurality of medical equipment operator as shown in FIG. 2G.

Further, the layouts of FIGS. 2C to 2H may be different User Interface (UI) designs for presenting different information on different devices according to the matching application. However, it is not intended to limit the contents or the layouts of the information of the present disclosure.

Figure 3A:
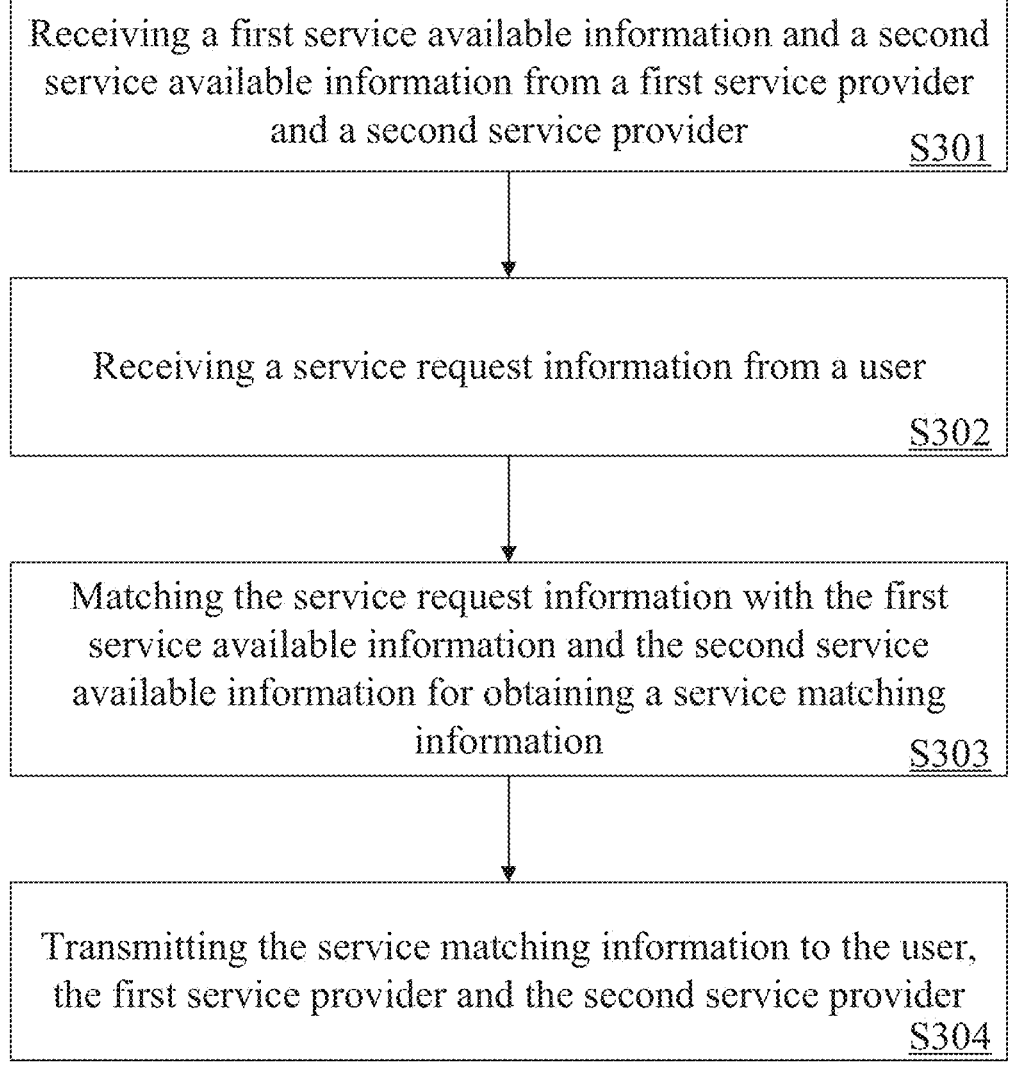

Some embodiments of the present disclosure include a method of service matching, and a flowchart diagram thereof is shown in FIG. 3A. The method of some embodiments is for use in a matching system (e.g., the matching system of the aforesaid embodiments). Detailed operations of the method are described below.

Operation S301 is executed to receive a first service available information and a second service available information from a first service provider and a second service provider respectively. Operation S302 is executed to receive a service request information from a user. S303 is executed to match the service request information with the first service available information and the second service available information for obtaining a service matching information. Operation S304 is executed to transmit the service matching information to the user, the first service provider and the second service provider.

Figure 3B:
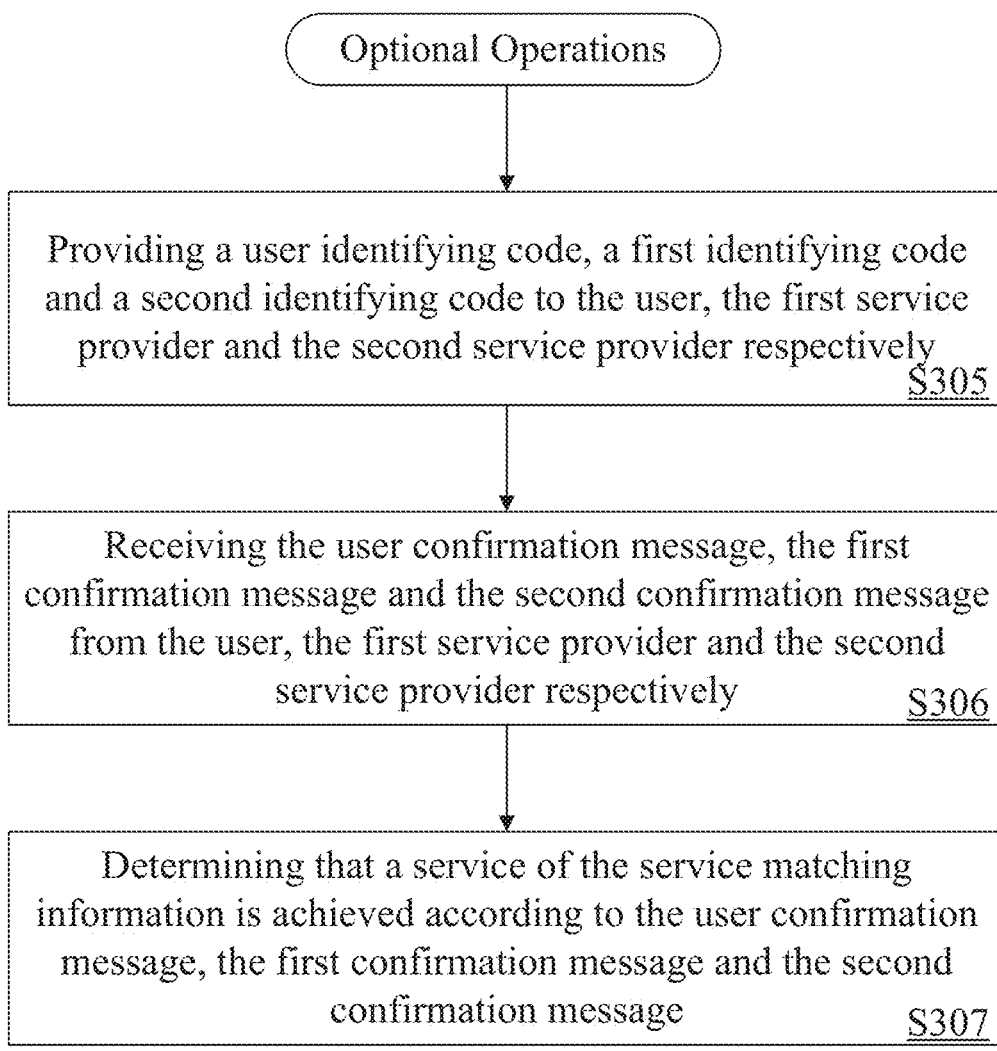

Please refer to FIG. 3B which is a flowchart diagram of some optional operations. In some embodiments, operation S305 is optionally executed to provide a user identifying code, a first identifying code and a second identifying code to the user, the first service provider and the second service provider respectively.

Accordingly, the user may generate a user confirmation message by scanning the first identifying code and the second identifying code. The first service provider may generate a first confirmation message by scanning the user identifying code and the second identifying code. The second service provider may generate a second confirmation message by scanning the user identifying code and the first identifying code.

Operation S306 is optionally executed to receive the user confirmation message, the first confirmation message and the second confirmation message respectively from the user, the first service provider and the second service provider. Operation S307 is optionally executed to determine that a service of the service matching information is achieved according to the user confirmation message, the first confirmation message and the second confirmation message.

Please refer to FIG. 3C which is a flowchart diagram of some optional operations. In some embodiments, operation S308 is optionally executed to receive a service comment information from one of the user, the first service provider and the second service provider. In some embodiments, the service matching information corresponds to a service equipment. Operation S309 is optionally executed to receive an equipment utilization log from the service equipment. The equipment utilization log is recorded by the service equipment.

Figure 4:
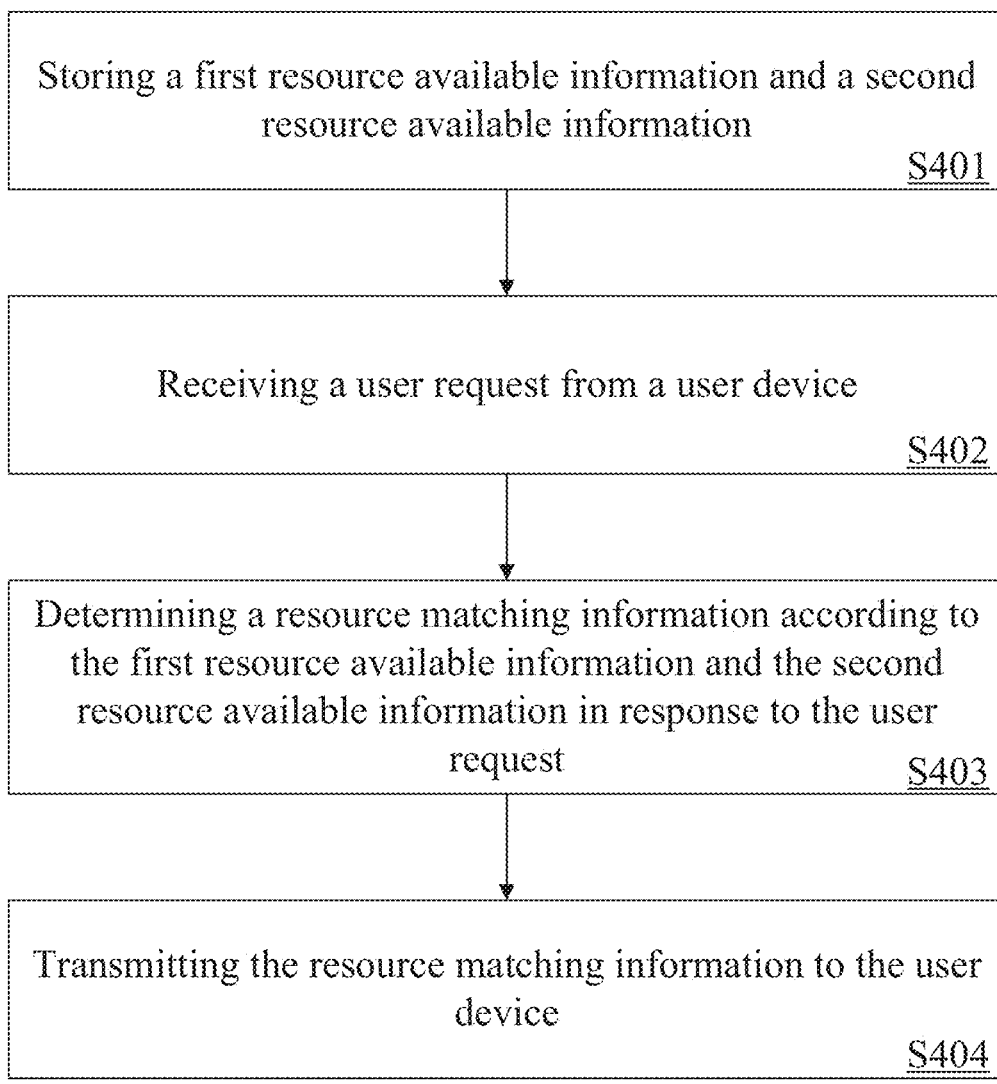
FIG. 4 is a flowchart diagram in accordance with some embodiments of the present disclosure.

Some embodiments of the present disclosure include a resource matching method, and a flowchart diagram thereof is shown in FIG. 4. The resource matching method of some embodiments is for use in a server of a matching system (e.g., the server and the matching system of the aforesaid embodiments). Detailed operations of the method are described below.

Operation S401 is executed to store, by the server, a first resource available information and a second resource available information. Operation S402 is executed to receive, by the server, a user request from a user device. Operation S403 is executed to determine, by the server, a resource matching information according to the first resource available information and the second resource available information in response to the user request. Operation S404 is executed to transmit, by the server, the resource matching information to the user device.

Figure 5A:
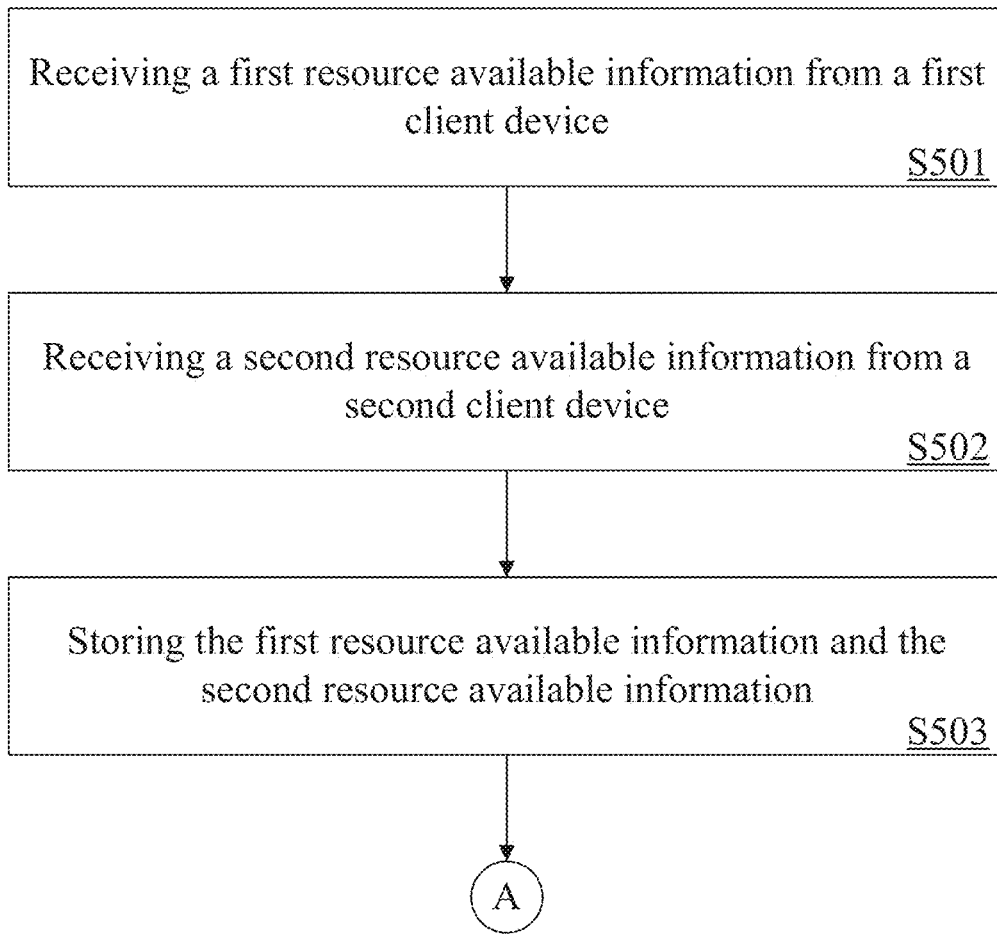
FIGS. 5A to 5D are flowchart diagrams in accordance with some embodiments of the present disclosure.
Figure 5B:
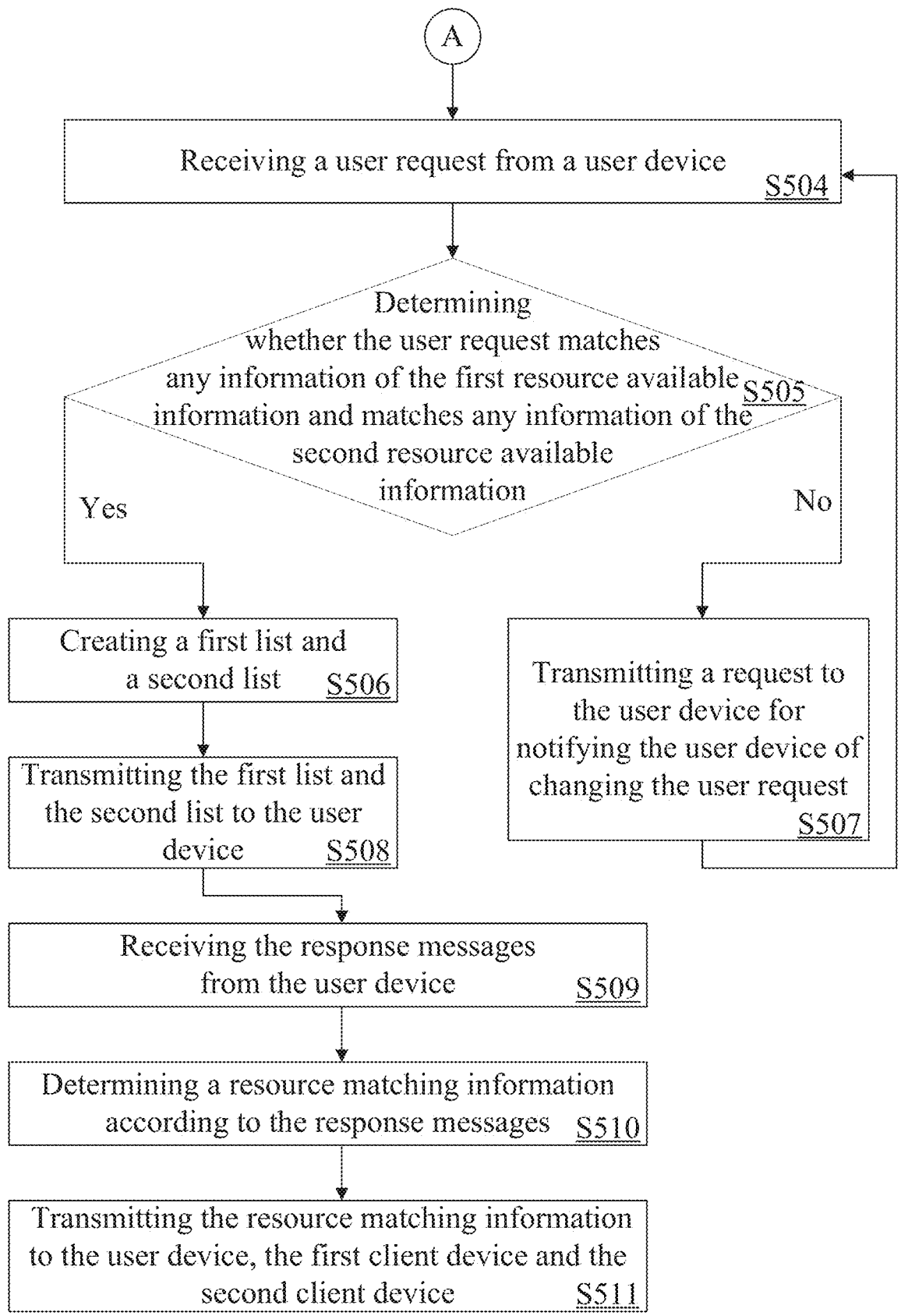

Some embodiments of the present disclosure include a resource matching method, and flowchart diagrams thereof are shown in FIG. 5A to 5B. The resource matching method of some embodiments is for use in a server of a matching system (e.g., the server and the matching system of the aforesaid embodiments). Detailed operations of the method are described below.

Operation S501 is executed to receive, by the server, a first resource available information from a first client device. Operation S502 is executed to receive, by the server, a second resource available information from a second client device. In some embodiments, operation S502 may be executed before operation S501.

In some embodiments, the first resource available information corresponds to an equipment owner identification, and the first resource available information includes a first equipment information, a plurality of location information and a plurality of time information. The first equipment information, the plurality of location information of the first resource available information and the plurality of time information of the first resource available information correspond to an equipment.

Further, the second resource available information corresponds to an equipment operator identification, and the second resource available information includes a second equipment information, a plurality of location information and a plurality of time information. The second equipment information, the plurality of location information of the second resource available information and the plurality of time information of the second resource available information correspond to the equipment.

Operation S503 is executed to store, by the server, the first resource available information and the second resource available information for later use. Operation S504 is executed to receive, by the server, a user request from a user device. The user request includes an equipment request, a location request and a time request.

Operation S505 is executed to determine, by the server, whether the user request matches any information of the first resource available information and matches any information of the second resource available information.

More specifically, if it is determined that: (1) the equipment request matches the first equipment information, the location request matches a first location information of the first resource available information and the time request matches a first time information of the first resource available information; and (2) the equipment request matches the second equipment information, the location request matches a second location information of the second resource available information and the time request matches a second time information of the second resource available information, operation S506 is executed to create, by the server, a first list and a second list based on the determination. Otherwise, operation S507 is executed to transmit, by the server, a request to the user device for notifying the user device of changing the user request.

In some embodiments, the equipment of the equipment owner identification corresponds to a first rank and the equipment operator identification corresponds to a second rank. In Operation S506, the first list is created based on the first rank, and the second list is created based on the second rank. In particular, the equipment of the equipment owner identification with the first rank is preferentially listed in the first list. The equipment operator identification with the second rank is preferentially listed in the second list.

After the first list and the second list are created, operation S508 is executed to transmit, by the server, the first list and the second list to the user device. Therefore, the user device selects the equipment with the equipment owner identification recorded on the first list and selects the equipment operator identification recorded on the second list. And then, the user device transmits response messages to the server for the selections.

Operation S509 is executed to receive, by the server, the response message from the user device. Operation S510 is executed to determine, by the server, a resource matching information according to the response messages. In detail, the resource matching information includes a user identification of the user device, the equipment owner identification, the equipment operator identification, a location matching information, a time matching information and an equipment matching information. Operation S511 is executed to transmit, by the server, the resource matching information to the user device, the first client device and the second client device.

Figure 5C:
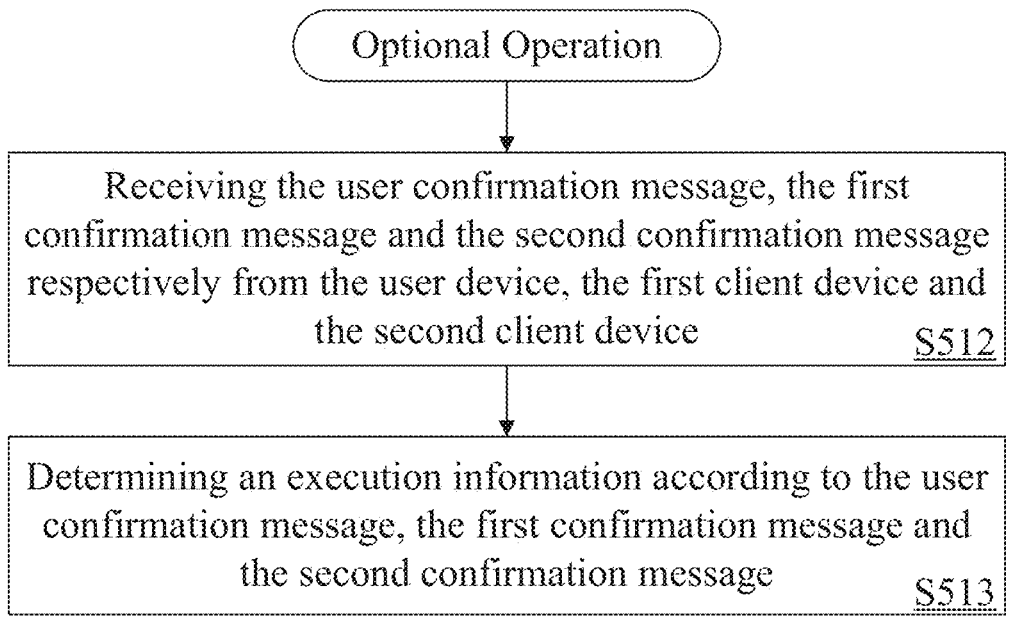

Please refer to FIG. 5C which is a flowchart diagram of some optional operations. In some embodiments, a user identifying code, a first identifying code and a second identifying code may be respectively provided in the resource matching information for the user device, the first client device and the second client device.

Therefore, the user device may scan the first identifying code of the first client device and the second identifying code of the second client device for generating a user confirmation message. The first client device may scan the user identifying code of the user device and the second identifying code of the second client device for generating a first confirmation message. The second client device may scan the user identifying code of the user device and the first identifying code of the first client device for generating a second confirmation message.

When the user confirmation message, the first confirmation message and the second confirmation message are transmitted back to the server, operation S512 is optionally executed to receive, by the server, the user confirmation message, the first confirmation message and the second confirmation message respectively from the user device, the first client device and the second client device. Operation S513 is executed to determine, by the server, an execution information according to the user confirmation message, the first confirmation message and the second confirmation message.

Figure 5D:
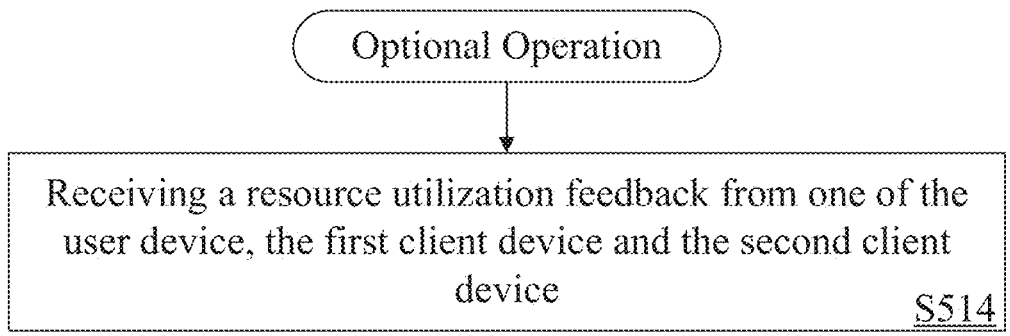
Figure 5D:
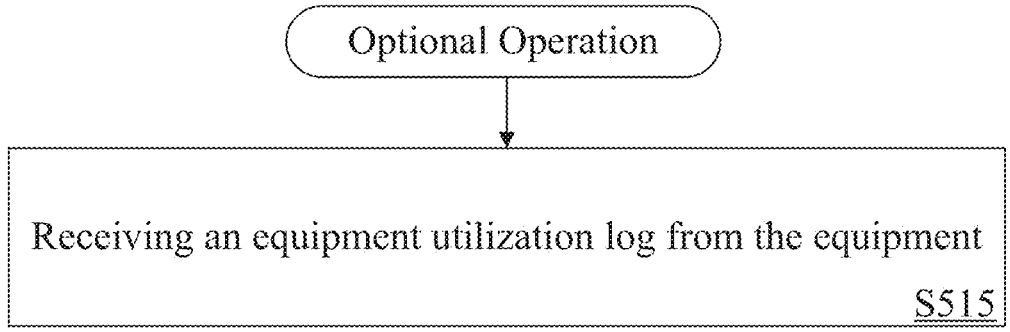

Please refer to FIG. 5D which is a flowchart diagram of some optional operations. Operation S514 is optionally executed to receive, by the server, a resource utilization feedback from one of the user device, the first client device and the second client device. Operation S515 is optionally executed to receive, by the server, an equipment utilization log from the equipment.

It shall be particularly appreciated that the processors mentioned in the above embodiments may be a central processing unit (CPU), other hardware circuit elements capable of executing relevant instructions, or combination of computing circuits that are well-known by those skilled in the art based on the above disclosures. Moreover, the transceivers mentioned in the above embodiments may be a combination of a network data transmitter and a network data receiver. The storage mentioned in the above embodiments may be memories, such as ROM, RAM, etc., for storing data. Further, the bus may a communication interface for transferring data between CPU and transceiver, and may include electrical bus interface, optical bus interface or even wireless bus interface. However, such description is not intended to limit the hardware implementation embodiments of the present disclosure Although the present disclosure and its advantages have been described in detail, it should be understood that various changes, substitutions and alterations can be made herein without departing from the spirit and scope of the disclosure as defined by the appended claims. For example, many of the processes discussed above can be implemented in different methodologies and replaced by other processes, or a combination thereof.

Moreover, the scope of the present application is not intended to be limited to the particular embodiments of the process, machine, manufacture, composition of matter, means, methods and steps described in the specification. As one of ordinary skill in the art will readily appreciate from the disclosure of the present disclosure, processes, machines, manufacture, compositions of matter, means, methods, or steps, presently existing or later to be developed, that perform substantially the same function or achieve substantially the same result as the corresponding embodiments described herein may be utilized according to the present disclosure. Accordingly, the appended claims are intended to include within their scope such processes, machines, manufacture, compositions of matter, means, methods, or steps.

What is claimed is:

1. A resource matching method for use in a server, the method comprising:
    storing, by the server, a first resource available information and a second resource available information, wherein the first resource available information corresponds to an equipment owner identification, the first resource available information comprises a first equipment information, a first location information and a first time information which correspond to an equipment;
    receiving, by the server, a user request from a user device, wherein the user request comprises an equipment request, a location request and a time request;
    determining, by the server, that the equipment request matches the first equipment information, the location request matches the first location information and the time request matches the first time information;
    creating, by the server, a first list based on the determination of that that the equipment request matches the first equipment information, the location request matches the first location information and the time request matches the first time information, wherein the first list records the equipment with the equipment owner identification;
    transmitting, by the server, the first list to the user device so that the user device selects the equipment and transmits a first response message;
    receiving, by the server, the first response message;
    determining, by the server, a resource matching information according to the first response message and the second resource available information in response to the user request; and
    transmitting, by the server, the resource matching information to the user device.

2. The method of claim 1, further comprising:
    receiving, by the server, the first resource available information from a first client device; and
    receiving, by the server, the second resource available information from a second client device.

3. The method of claim 2, wherein transmitting the resource matching information further comprises:
    transmitting, by the server, the resource matching information to the user device, the first client device and the second client device.

4. The method of claim 3, further comprising:
    receiving, by the server, a user confirmation message, a first confirmation message and a second confirmation message respectively from the user device, the first client device and the second client device; and
    determining, by the server, an execution information according to the user confirmation message, the first confirmation message and the second confirmation message.

5. The method of claim 3, further comprising:
    receiving, by the server, a resource utilization feedback from one of the user device, the first client device and the second client device.

6. The method of claim 1, wherein the second resource available information corresponds to an equipment operator identification, the second resource available information further comprises a second equipment information, a second location information and a second time information, and the method further comprises:
    determining, by the server, that the equipment request matches the second equipment information, the location request matches the second location information and the time request matches the second time information;
    creating, by the server, a second list based on the determination of that that the equipment request matches the first equipment information, the location request matches the first location information and the time request matches the first time information, wherein the second list records the equipment operator identification;
    transmitting, by the server, the second list to the user device so that the user device selects the equipment operator identification and transmits a second response message; and
    receiving, by the server, the second response message.

7. The method of claim 6, wherein determining the resource matching information further comprises:
    determining, by the server, the resource matching information according to the first response message and the second response message, wherein the resource matching information comprises a user identification of the user device, the equipment owner identification, the equipment operator identification, a location matching information, a time matching information and an equipment matching information.

8. The method of claim 6, wherein the equipment of the equipment owner identification corresponds to a first rank, the equipment operator identification corresponds to a second rank, the first list is created based on the first rank, and the second list is created based on the second rank.

9. The method of claim 1, wherein the resource matching information corresponds to an equipment, and the method further comprises:
    receiving, by the server, an equipment utilization log from the equipment.

10. A server for resource matching, comprising:
    a storage for storing a first resource available information and a second resource available information, wherein the first resource available information corresponds to an equipment owner identification, the first resource available information comprises a first equipment information, a first location information and a first time information which correspond to an equipment;
    a transceiver for receiving a user request from a user device, wherein the user request comprises an equipment request, a location request and a time request; and
    a processor being electrically coupled to the storage and the transceiver, and for:
        determining that the equipment request matches the first equipment information, the location request matches the first location information and the time request matches the first time information;

creating a first list based on the determination of that that the equipment request matches the first equipment information, the location request matches the first location information and the time request matches the first time information, wherein the first list records the equipment with the equipment owner identification;

wherein the transceiver further:

transmits the first list to the user device so that the user device selects the equipment and transmits a first response message; and receives the first response message;

wherein the processor further determines a resource matching information according to the first response message and the second resource available information in response to the user request;

wherein the transceiver further transmits the resource matching information to the user device.

11. The server of claim 10, wherein the transceiver further:

receives the first resource available information from a first client device;

receives the second resource available information from a second client device; and transmits the resource matching information to the user device, the first client device and the second client device.

12. The server of claim 11, wherein the transceiver further:

receives a user confirmation message, a first confirmation message and a second confirmation message respectively from the user device, the first client device and the second client device;

wherein the processor further:

determines an execution information according to the user confirmation message, the first confirmation message and the second confirmation message.

13. The server of claim 10, wherein the second resource available information corresponds to an equipment operator identification, the second resource available information further comprises a second equipment information, a second location information and a second time information, and the processor further:

determines that the equipment request matches the second equipment information, the location request matches the second location information and the time request matches the second time information; and creates a second list based on the determination of that that the equipment request matches the first equipment information, the location request matches the first location information and the time request matches the first time information, wherein the second list records the equipment operator identification;

wherein the transceiver further:

transmits the second list to the user device so that the user device selects the equipment operator identification and transmits a second response message; and receives the second response message.

14. The server of claim 10, wherein the resource matching information corresponds to an equipment, and the transceiver further:

receives an equipment utilization log from the equipment.

* * * * *